United States Patent
Van Asseldonk et al.

(10) Patent No.: US 12,059,513 B2
(45) Date of Patent: *Aug. 13, 2024

(54) BREAST PUMP DEVICE

(71) Applicant: KONINKLIJKE PHILIPS N.V., Eindhoven (NL)

(72) Inventors: Johannes Petrus Antonius Maria Van Asseldonk, Best (NL); Arnold Aalders, Sprang Capelle (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/939,329

(22) Filed: Sep. 7, 2022

(65) Prior Publication Data

US 2023/0059967 A1    Feb. 23, 2023

Related U.S. Application Data

(63) Continuation of application No. 16/487,218, filed as application No. PCT/EP2018/054719 on Feb. 27, 2018, now Pat. No. 11,464,890.

(30) Foreign Application Priority Data

Feb. 27, 2017    (EP) ..................... 17158158

(51) Int. Cl.
*A61M 1/06*    (2006.01)

(52) U.S. Cl.
CPC .............. *A61M 1/06* (2013.01); *A61M 1/062* (2014.02); *A61M 1/06935* (2021.05);
(Continued)

(58) Field of Classification Search
CPC ............................................. A61M 1/06–069
See application file for complete search history.

(56) References Cited

U.S. PATENT DOCUMENTS

| | | | |
|---|---|---|---|
| 4,857,051 A | 8/1989 | Larsson | |
| 5,071,403 A * | 12/1991 | Larsson | A61M 1/06 604/320 |

(Continued)

FOREIGN PATENT DOCUMENTS

| | | |
|---|---|---|
| DE | 2949654 | 7/1981 |
| GB | 686367 | 1/1953 |

(Continued)

OTHER PUBLICATIONS

International Search Report and Written Opinion Dated May 28, 2018 for International Application No. PCT/EP2018/054719 Filed Feb. 27, 2018.

*Primary Examiner* — Courtney B Fredrickson

(57) ABSTRACT

A breast pump device (1) comprises an expression kit (2), a vacuum unit (3), and a conduit (5) for establishing an air path between an air outlet (27) of the expression kit (2) and an air inlet (35) of the vacuum unit (3). The expression kit (2) is equipped with a barrier portion (26) for preventing milk leakage from the expression kit (2) towards the hose (5) and the vacuum unit (3). In case some droplets of milk enter the barrier portion (26) and/or drawn through the barrier portion (26) by an ongoing pumping action, aspects of the behavior of the motor (32) for driving the pump (31) are influenced, and the insight that this happens is used for terminating operation of the motor (32) as soon as a too large deviation of one or more operational characteristics of the motor (32) with respect to a reference is found.

21 Claims, 1 Drawing Sheet

(52) U.S. Cl.
CPC ....... *A61M 1/0697* (2021.05); *A61M 2205/07* (2013.01); *A61M 2205/103* (2013.01); *A61M 2205/3317* (2013.01); *A61M 2205/3365* (2013.01); *A61M 2205/52* (2013.01); *A61M 2205/7536* (2013.01)

(56) References Cited

U.S. PATENT DOCUMENTS

| | | | |
|---|---|---|---|
| 6,110,141 | A | 8/2000 | Nueesch |
| 9,333,283 | B2 | 5/2016 | Cook |
| 2001/0044593 | A1* | 11/2001 | Lundy ...................... A41C 3/04 604/74 |
| 2001/0047148 | A1* | 11/2001 | Suh ........................ A61M 1/82 604/74 |
| 2002/0072701 | A1 | 6/2002 | Nuesch |
| 2015/0190560 | A1 | 7/2015 | Aalders |
| 2015/0209497 | A1* | 7/2015 | Aalders .................. A61M 1/74 604/74 |
| 2016/0287767 | A1 | 10/2016 | Simmons |
| 2016/0367754 | A1* | 12/2016 | Alderete, Jr. ............. F04B 7/04 |
| 2017/0072119 | A1 | 3/2017 | Aalders |

FOREIGN PATENT DOCUMENTS

| | | | |
|---|---|---|---|
| IN | 202366231 U | 8/2012 | |
| WO | 00/41745 | 7/2000 | |
| WO | 2012/037724 | 3/2012 | |
| WO | 2015/150225 | 10/2015 | |
| WO | WO-2015150225 A1 * | 10/2015 | ............. A61M 1/06 |
| WO | 2016/156173 | 10/2016 | |

* cited by examiner

BREAST PUMP DEVICE

CROSS REFERENCE TO RELATED APPLICATIONS

This application is a Continuation of U.S. patent application Ser. No. 16/487,218 filed Aug. 20, 2019, which is the U.S. National Phase application under 35 U.S.C. § 371 of International Application No. PCT/EP2018/054719 filed Feb. 27, 2018, published as WO 2018/154127 on Aug. 30, 2018, which claims the benefit of European Patent Application Number 17158158.0 filed Feb. 27, 2017. These applications are hereby incorporated by reference herein.

FIELD OF THE INVENTION

The invention relates to a breast pump device for extracting breast milk from a human breast, comprising: an expression kit comprising a breast-receiving funnel, a milk outlet, an air outlet, and a milk leakage preventing arrangement associated with the air outlet, constituting a barrier to human breast milk while allowing air to pass; a vacuum unit comprising an air inlet, a pump for sucking air from the breast-receiving funnel of the expression kit, through the air outlet of the expression kit and the air inlet of the vacuum unit, and an electric motor for driving the pump; a conduit for establishing an air path between the air outlet of the expression kit and the air inlet of the vacuum unit; and a control system for controlling operation of the motor for driving the pump, particularly for controlling a supply of electric power to the motor.

BACKGROUND OF THE INVENTION

A breast pump device as mentioned in the opening paragraph is known from WO 2015/150225 A1, for example.

In general, breast pump devices are well known devices for extracting milk from a breast of a user, or two breasts simultaneously. A breast pump device may be used if the baby or infant is not itself able to extract milk from the breast, or if the mother is separated from the baby or infant, and the baby or infant is to be fed with breast milk by someone else. In other words, breast pump devices are used by mothers to express breast milk at a convenient time, to be stored for later consumption by their child. A breast pump device may also be helpful in a situation in which it is desired to stimulate and increase milk production in women with a low milk supply.

A breast pump device is typically operated with one or two expression kits. Among other things, an expression kit comprises a breast-receiving funnel for receiving a user's breast, which funnel may be equipped with pads or the like for massaging the breast in a certain way, and is designed for connection to a vacuum unit for generating a pressure cycle in the breast-receiving funnel, by means of which milk expression from the breast is enabled. In practical cases, the vacuum unit comprises an electric vacuum pump. The fact is that by generating a pressure cycle, particularly a vacuum cycle, possibly accompanied by a certain way of massaging the breast, a simulation of a feeding action is obtained, which triggers the necessary let-down reflex in the user of the breast pump device. For the sake of completeness, it is noted that the term "vacuum" as used in this text refers to a negative pressure with respect to ambient pressure, i.e. a pressure that is significantly lower than ambient pressure.

For hygienic reasons, most breast pump devices are equipped with a milk leakage preventing arrangement that is configured and arranged such as to act as a barrier between the breast and the vacuum unit. According to a known option, such an arrangement may be provided as a non-permeable resilient silicone diaphragm, which needs to make a stroke for the purpose of creating a vacuum at the breast. The pump of the vacuum unit is operated to cause the diaphragm to flex, thereby expanding the air in the breast-receiving funnel and creating the required vacuum at the breast as a result thereof. When the vacuum at the pump side is released, the diaphragm will move back to its rest position. As the vacuum at the pump is indirectly causing the vacuum at the breast, the hygienic function of the diaphragm is implemented. This concept is well-established and has been used in the field of breast pump devices for many years.

According to an alternative option allowing for a simplified design of a breast pump device, milk leakage preventing arrangements which are capable of blocking human breast milk while allowing air to pass are applied. For example, such arrangements may comprise a sheet of material being provided with holes, a porous membrane, or a labyrinth. WO 2015/150225 A1 discloses a milk leakage preventing arrangement comprising a breathable membrane that is gas-permeable and liquid-impermeable, and that has hydrophobic properties.

It appears in practice that although the milk leakage preventing arrangements mentioned in the preceding paragraph are designed to block human breast milk while allowing air to pass, it may still happen that a very small volume of milk passes the arrangement. Various measures aimed at preventing such a small volume of milk from contaminating the vacuum unit are known in the art. In this respect, it is noted that WO 00/41745 discloses a breast pump device including an overflow sensor and an automated flushing system, wherein the overflow sensor serves for detecting the presence of milk entering the internal pump mechanisms, and instantly shuts off the pump to prevent contamination, and wherein the automated flushing system provides a series of specifically timed cleaning actions of the pump. WO 2012/037724 A1 relates to the use of a safety device including a liquid collecting box in a breast pump device. The liquid collecting box is arranged at a position between the expression kit and the vacuum unit, and is equipped with a control unit and a sensing unit. When liquid is detected, the sensing unit can output a detection signal to the control unit for activating the control unit to produce sound and light, or for switching off the pump. GB 686,367 discloses a breast pump device having a vacuum pump of the type comprising a piston and a cylinder, and furthermore having an air relief valve connected to the pump, for the escape of any enclosed air, and a chamber at the end of the cylinder to trap any milk that might otherwise be sucked towards the vacuum pump and eventually reach the interior of the cylinder. One of two opposite walls of the chamber may also be the end wall of the cylinder and the other of the opposite walls may be made of transparent material for visual inspection of the interior of the chamber.

SUMMARY OF THE INVENTION

It is an object of the invention to provide measures for preventing milk that has leaked through the air outlet of the expression kit from reaching the vacuum unit, and to thereby avoid an unhygienic situation, as an advantageous alternative or addition to known measures for keeping the hygiene of a breast pump device at an acceptable level.

According to the invention, a breast pump device as defined in the opening paragraph is provided, the control system of the breast pump device being configured to detect at least one operational characteristic of the motor, to make a comparison between the detected at least one operational characteristic and a reference of the at least one operational characteristic throughout operation of the breast pump device, and to terminate power supply to the motor when it follows from the comparison that a deviation of the at least one operational characteristic from the reference is larger than a predetermined maximum deviation.

It follows from the foregoing definition that the breast pump device according to the invention is configured to monitor functioning of the electric motor for driving the pump, during the time that the motor is operated, and to shut off the motor when at least one operational characteristic of the motor appears to deviate from a reference of the at least one operational characteristic to a too large extent. By having the specific configuration of the control system of the breast pump device as defined in the foregoing, it is possible to determine at any time during operation whether motor behavior is as expected, or not. If not, this is taken as an indication that something in the breast pump device is not as expected, which is the case when milk clogs the milk leakage preventing arrangement associated with the air outlet of the expression kit and/or milk has passed the milk leakage preventing arrangement and is at a position somewhere between the air outlet of the expression kit and the air inlet of the vacuum unit, which may be a position in the conduit, for example.

An important advantage associated with the breast pump device according to the invention is that automatic detection of extraordinary conditions of the breast pump device is performed during operation thereof, so that the motor may be shut off automatically as soon as deviations are found, wherein the detection is done by checking one or more operational characteristics of the motor. In particular, the control system of the breast pump device may be configured to detect at least one of an electric current drawn by the motor and a rotational speed of the motor. Detecting at least one operational characteristic of the motor is a reliable and safe process, contrary to detecting the presence of liquid at a certain position, as in the latter case, the sensor(s) used in the process are susceptible to contamination. In respect of the conventional use of one or more sensors, it is furthermore noted that sensors require power, as a result of which power cables need to be provided. Obviously, the positioning of such cables involves design and usability challenges.

The invention is based on the insight that there are several ways in which the motor behavior can be influenced by a condition of the breast pump device. The fact is that the motor drives the pump to generate vacuum, and that normally a release valve for releasing the vacuum is used as well, so as to be able to have a continuous process in which vacuum is alternately generated and released. In any case, the pump is designed to evacuate a certain air volume in a certain time, and the control system expects a certain load of the motor. When milk clogs (part of) the milk leakage preventing arrangement and/or is present somewhere between the air outlet of the expression kit and the air inlet of the vacuum unit, the air volume that is evacuated is drastically reduced, resulting in a swift increase of vacuum at the pump side, which may even lead to stalling of the pump. In such a case, the voltage supplied to the motor is not sufficient to keep the pump rotating, and the motor draws an increasing amount of electric current. One of the possibilities offered by the invention is to detect whether such an increase of the current drawn by the motor occurs, and if this is found to be the case, to terminate power supply to the motor.

Another possibility existing within the framework of the invention involves monitoring the current curve of the motor. In that case, an all too large deviation of the actual current curve from a reference current curve may be taken as an indication of a stalling pump. This possibility is found on the basis of the insight that the current behavior of the motor is linked to the flow behavior of the pump, that one of the determining factors of the flow behavior of the pump is pressure, and that pressure is related to air volume. Thus, when the air volume changes (decreases) drastically, a deviating current curve is obtained. In respect of the reference current curve, it is noted that this curve is determined by the voltage supplied to the motor. In general, assuming a certain input voltage and a normal condition of the breast pump device, which involves a certain air volume to be evacuated by the pump, it is possible to define expected motor behavior, particularly expected current behavior and/or expected rotational speed behavior.

Another possibility existing within the framework of the invention is applicable to the situation in which the pump continues to operate during vacuum release. Normally, a typical vacuum release curve can be expected. However, when the vacuum is influenced as a result of milk clogging (part of) the milk leakage preventing arrangement and/or being present somewhere between the air outlet of the expression kit and the air inlet of the vacuum unit, the vacuum release curve is different from what would normally be expected. In particular, in such a case, the vacuum will release very fast, resulting in an increase of the rotational speed of the motor when the input voltage is kept constant.

Generally speaking, the control system of the breast pump device according to the invention may be configured to determine an actual value of the reference of the at least one operational characteristic in relation to an actual input voltage of the motor. Alternatively, the control system may be configured to use a detected value of the at least one operational characteristic as a reference for a next detected value of the at least one operational characteristic, in which case the control system is suitable for checking whether an increase of the at least one operational characteristic occurs.

As explained in the foregoing, the reference may involve a curve of the at least one operational characteristic over time, and the control system may be configured to determine a curve of the detected at least one operational characteristic over time, to make a comparison of the detected curve and the reference curve, and to terminate power supply to the motor when it follows from the comparison that a deviation of the detected curve from the reference curve is larger than a predetermined maximum deviation. The control system may furthermore be configured to determine the reference curve of the at least one operational characteristic over time in relation to an input voltage curve of the motor over time.

In practical embodiments of the breast pump device, the control system may comprise a microcontroller, which may be capable of retrieving preprogrammed information from a memory, wherein the preprogrammed information may be available in the form of a look-up table, for example, and/or which may be capable of following preprogrammed algorithms. In the context of the invention, the preprogrammed information is related to the reference of the at least one operational characteristic of the motor, and also to the maximum allowable deviation between the reference of the at least one operational characteristic and the detected at least one operational characteristic.

In an advantageous and practical embodiment, the breast pump device according to the invention comprises at least one milk collector for receiving and collecting any milk leaking from the expression kit, the milk collector being located beyond the milk leakage preventing arrangement associated with the air outlet of the expression kit, as seen from the breast-receiving funnel of the expression kit. Using at least one milk collector offers the opportunity to catch small volumes of milk and to thereby avoid contamination of the vacuum unit, and also guarantees that there is sufficient time for detecting unexpected motor behavior and shutting off the motor. For example, assuming that the breast pump device comprises connectors for arrangement at the respective ends of the conduit, the one connector being configured to connect the conduit in an airtight manner to the air outlet of the expression kit, and the other connector being configured to connect the conduit in an airtight manner to the air inlet of the vacuum unit, it may be practical for at least one of the connectors to comprise a room that is suitable for receiving and collecting milk, i.e. a room constituting a milk collector. In such a case, the at least one connector comprising the milk collector may be designed for having the room of the connector located at a lower level than an area of the connector that is configured to connect the connector to the conduit, so that it is achieved that any milk can simply fall down in the room under the influence of gravity. Furthermore, it may be so that the connector that is configured for connecting the conduit in an airtight manner to the air inlet of the vacuum unit is designed to connect to the conduit at a central area thereof, and that the air inlet of the vacuum unit is arranged at a higher level than a center of an area of the vacuum unit that is configured to receive the connector, so that when the connector and the conduit are in place with respect to the vacuum unit, an offset configuration of the conduit and the air inlet of the vacuum unit is realized, in which milk may fall down in the connector while air finds its way to the inside of the vacuum unit through the air inlet thereof.

The at least one connector comprising the milk collector may be at least partially made of a transparent material, so as to have a possibility of a user visually inspecting the milk collector, in which case a user can readily determine if a presence of milk in the milk collector is the reason of an automatic termination of operation of the breast pump device, and if the connector needs emptying/cleaning.

In conformity with the information provided with the explanation of the prior art, it is noted that it is practical for the milk leakage preventing arrangement associated with the air outlet of the expression kit to be hydrophobic and to comprise one of a solid sheet of material, the sheet being provided with holes, a porous membrane, and a labyrinth. A practical example of the conduit for establishing the necessary air path between the air outlet of the expression kit and the air inlet of the vacuum unit is a flexible hose.

The above-described and other aspects of the invention will be apparent from and elucidated with reference to the following detailed description of an embodiment of a breast pump device comprising an expression kit for application to a breast and a vacuum unit that is connectable to the expression kit through a hose and that serves for generating a pressure cycle by means of which milk expression from the breast is enabled.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
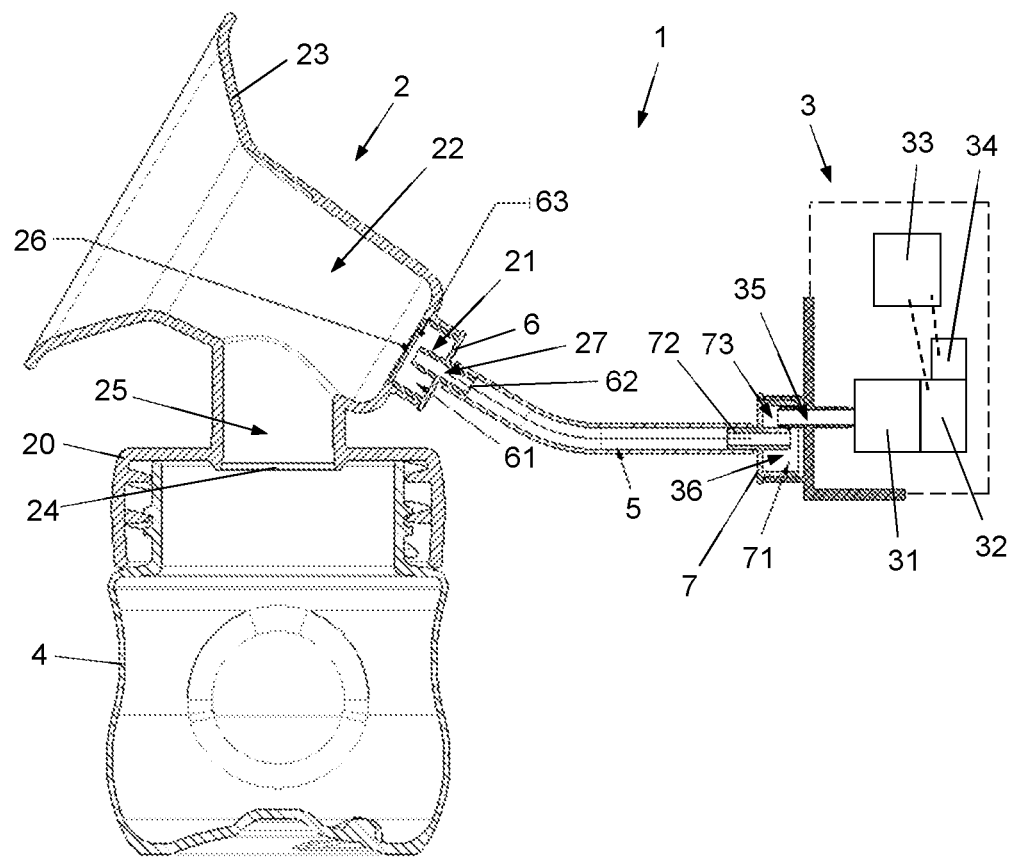
FIG. 1 diagrammatically shows a breast pump device according to the invention, comprising an expression kit and a vacuum unit connected to the expression kit through a hose, wherein the expression kit, the hose and connectors as located at both ends of the hose, and a connection part of the vacuum unit are shown in a sectional view, and wherein a vacuum pump, a motor of the vacuum pump, a controller, and a sensor, which are components of the vacuum unit, are represented by blocks.
Figure 2:
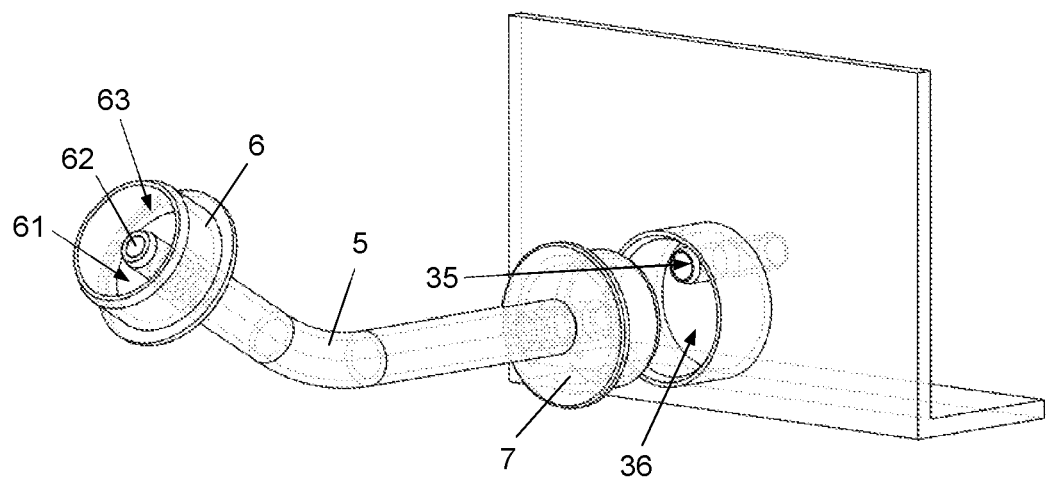
FIG. 2 diagrammatically shows a perspective view of the assembly of the hose and the connectors, and the connection part of the vacuum unit, wherein the assembly of the hose and the connectors is shown separately from the connection part of the vacuum unit.

FIGS. 1 and 2 relate to a breast pump device 1 according to the invention, comprising an expression kit 2 and a vacuum unit 3 for generating a pressure cycle during which vacuum is alternately created and released. The expression kit 2 comprises a breast pump body 20 and a milk receptacle 4 which is connectable to the breast pump body 20, e.g. by screwing, thereby closing a lower end of the breast pump body 20. The vacuum unit 3 is an electric vacuum unit and comprises a pump 31, an electric motor 32 for driving the pump 31, and a controller 33 for controlling operation of the motor 32. Practical aspects of the vacuum unit 3, such as the mechanical connection of the pump 31 to the motor 32, and the electric connection of the motor 32 to a source of electric power, which may be the mains or a battery, for example, will not be deliberated on here as such aspects are known in the field of breast pump devices and may be conventional in the framework of the invention.

In FIG. 1, the breast pump device 1 is shown in an assembled condition, in which the vacuum unit 3 is connected to the expression kit 2 through a hose 5. Such a configuration allows for a remote arrangement of the vacuum unit 3 with respect to the expression kit 2, so that the size of that part of the breast pump device 1 which is to be applied to a user's breast can be kept within reasonable limits. At one end, the hose 5 is connected to the expression kit 2 through a suitable connector 6 arranged at that particular end, which will hereinafter be referred to as expression kit connector 6. Likewise, at the other end, the hose 5 is connected to the vacuum unit 3 through a suitable connector 7 arranged at that particular end, which will hereinafter be referred to as vacuum unit connector 7. The breast pump body 20 of the expression kit 2 has a first pressure chamber 21 and a second pressure chamber 22. The first pressure chamber 21 is configured for receiving the expression kit connector 6.

It is to be noted that the breast pump device 1 can comprise two expression kits 2 for enabling a user of the breast pump device 1 to extract milk from two breasts at the same time, in which case the expression kits 2 can share a common vacuum unit 3.

The second pressure chamber 22 comprises a breast-receiving funnel 23, an aperture acting as a milk outlet 24, and a milk path 25 from the breast-receiving funnel 23 to the milk outlet 24. The breast-receiving funnel 23 is thus in fluid communication with the milk outlet 24 through the milk path 25. Optionally, a one-way valve is arranged at the milk outlet 24, for letting breast milk pass from the second pressure chamber 22 to the milk receptacle 4. The breast-receiving funnel 23 can comprise a massage cushion or the like (not shown) for providing a soft and warm feel to the breast and/or imitating a baby's sucking action. In the shown example, the first pressure chamber 21 is located at a backside of the breast-receiving funnel 23. Within the framework of the invention, other locations of the first pressure chamber 21 are possible, including a location at the milk receptacle 4 in case there is no valve at the milk outlet 24.

The first pressure chamber 21 and the second pressure chamber 22 are separated at the position of a barrier portion 26 that is located in the breast pump body 20. The barrier portion 26 is designed to function as a milk leakage preventing arrangement at the position of an air outlet 27 of the expression kit 20 and may be realized as a solid sheet being provided with a number of holes having dimensions in the micrometer range, or as a porous membrane or a labyrinth, for example. Furthermore, at least at the position of the barrier portion 26, the material of the breast pump body 20 may have hydrophobic properties. In any case, it is intended for the barrier portion 26 to serve as an arrangement in the breast pump device 1 that is air-permeable and liquid-impermeable, at a position associated with the very position where air flows out of the expression kit 2 in the direction of the vacuum unit 3 during operation of the breast pump device 1. In that way, it is achieved that the barrier portion 26 serves for separating the first pressure chamber 21 from the milk path 25 in the second pressure chamber 22, thereby increasing the level of hygiene of the breast pump device 1 and preventing liquid from reaching the hose 5 and the vacuum unit 3, while allowing for air communication between the first pressure chamber 21 and the second pressure chamber 22, at least to such an extent that the breast milk expression functionality of the breast pump device 1 is not hampered, assuming that the barrier portion 26 provides a sufficiently low pneumatic restriction to the air flow. For example, a vacuum applied to the first pressure chamber 21 also causes vacuum in the second pressure chamber 22 since air can pass through the barrier portion 26, whereas water and/or breast milk in the second pressure chamber 22 are blocked. Thereby, the barrier portion 26 acts as a hygienic shield. Having a hydrophobic barrier portion 26 may further positively influence bacteria-related aspects of the breast pump device 1, such that bacteria transfer to the hose 5 and the vacuum unit 3 are prevented.

It is possible for the breast pump body 20 to be equipped with a splash guard (not shown) arranged in the second pressure chamber 22 for shielding the barrier portion 26 from droplets of breast milk. Thereby, such a splash guard can act as a first barrier which avoids that too much breast milk reaches the barrier portion 26. Droplets of breast milk which reach the barrier portion 26 anyway can clear off the barrier portion 26 automatically in case the barrier portion 26 is hydrophobic. Advantageously, the entire breast pump body 20 is made of one single material, preferably a clear plastic material having hydrophobic properties, such as polymethylpentene (PMP) or polypropylene (PP).

General operational aspects of the breast pump device 1 will now be mentioned. In the first place, a user makes sure that the expression kit 2 and the vacuum unit 3 are properly connected to each other through the hose 5 and the connectors 6, 7. Before the vacuum unit 3 is activated, the user furthermore needs to take care that the milk receptacle 4 is properly connected to the breast pump body 20, and that the breast to be subjected to a milk extraction process is properly inserted into the breast-receiving funnel 23 of the second pressure chamber 22. In that situation, a breast-receiving end of the second pressure chamber 22 is sealingly closed by the breast, whereas a lower end of the second pressure chamber 22 is sealingly closed by the milk receptacle 4. When, starting from that situation, the vacuum unit 3 is activated, a pressure cycle involving generation and release of vacuum is realized in the first pressure chamber 21, as a result of which the breast is subjected to forces which serve for simulating a feeding situation, as a result of which milk supply is induced from the breast, and during which it happens that air is sucked in the first pressure chamber 21 from the second pressure chamber 22 through the barrier portion 26. A desired pressure profile, i.e. a time-variable pressure, can be applied to the breast taking into account the pneumatic restriction of the barrier portion 26. The breast milk flows from the breast-receiving funnel 23 to the milk receptacle 4 through the milk path 25 and the milk outlet 24, under the influence of gravity and/or the pressure generated by the vacuum unit 3.

According to the invention, in view of a practical possibility that despite the use of a milk leakage preventing arrangement comprising a barrier portion 26 in the breast pump device 1, it may accidentally happen that a few droplets of milk end up on the barrier portion 26, have a clogging effect on the barrier portion 26 and/or eventually pass to the pump side of the barrier portion 26, measures are taken in order to prevent milk from reaching the inside of the vacuum unit 3. These measures involve a configuration of the controller 33 that is aimed at performing a process of monitoring behavior of the motor 32 for driving the pump 31 and stopping operation of the motor 32 as soon as an abnormality is found in the behavior of the motor 32. Within the framework of the invention, many ways exist for performing such a process. In any case, suitable means such as a sensor 34 may be used for detecting at least one operational characteristic of the motor 32 and transmitting detected information to the controller 33 which is preprogrammed to process the detected information in a suitable manner. In particular, the controller 33 is configured to make a comparison between the detected information and an appropriate reference, and to terminate power supply to the motor 32 as soon as the comparison shows that a deviation of the detected information from the reference is larger than an allowable maximum. Naturally, if the motor behavior appears to be within limits of what normally might be expected, there is no need for action aimed at automatically shutting off the motor. In FIG. 1, the interaction between the motor 32, the controller 33 and the sensor 34 is diagrammatically indicated by means of dashed lines.

Examples of operational characteristics of the motor 32 that may be monitored include the electric current drawn by the motor 32 and a rotational speed of the motor 32. A clogging effect of milk on the barrier portion 26 and or a presence of milk somewhere between the barrier portion 26 and the vacuum unit 3 may cause the motor 32 to stall, as the motor 32 is only allowed to evacuate a smaller volume of air than the volume that is normally expected. In the art of electric motors, it is a known fact that when a motor stalls, the current drawn by the motor increases significantly. Thus, a possibility existing within the framework of the invention is to detect the current drawn by the motor and to assess whether the current is higher than may be expected and/or increases at a high rate. Also, taking into account the voltage supplied to the motor 32, the current curve can be monitored and compared to a reference that is appropriate in view of the voltage. In such a case, the controller 33 is used to switch off the motor 32 when the detected current curve appears to deviate from the reference current curve to a too large extent.

Besides relying on measurements of the current drawn by the motor 32, it is also possible to detect the rotational speed of the motor. Assuming that the voltage supplied to the motor 32 is kept constant, an increase of the rotational speed indicates that there are abnormalities in the pressure cycle, and thus, information about the rotational speed may be used for stopping the motor 32. For the purpose of detecting the rotational speed of the motor 32, the motor 32 may be equipped with a suitable RPM sensor.

Advantages of automatically terminating operation of the motor 32 are that it is not necessary to involve the user of the breast pump device 1 in a process of keeping watch if the device is functioning correctly. Also, as it takes some time for milk drawn through the barrier portion 26 to travel towards the vacuum unit 3, due to the length of the hose 5, a completely safe process is realized, in which the motor 32 can be stopped in time in order to terminate a sucking effect on the milk. Safety can even be further enhanced by designing at least one of the connectors 6, 7 in such a way that milk reaching the respective connector 6, 7 is retained in the connector 6, 7 and is thereby stopped from travelling further downstream towards the vacuum unit 3. In the shown example, both connectors 6, 7 are designed for having a milk collector 61, 71 in the form of a room that is available in the connector 6, 7, as will now be explained. For the sake of completeness, it is noted that in case the breast pump device 1 is equipped with one or more milk collectors, it is not essential for the milk collector(s) to be arranged in at least one of the connectors 6, 7.

In the shown example, the expression kit connector 6 comprises an air tube 62 extending from an inside space 63 of the connector 6 to outside of the connector 6. Interconnecting the hose 5 and the expression kit connector 6 involves inserting the air tube 62 in an end of the hose 5. When the connector 6 is arranged on the expression kit 2 and the breast pump device 1 is operated, air that is drawn from the breast-receiving funnel 23 passes the barrier portion 26 and enters the hose 5 through the air tube 62 of the connector 6. As the air tube 62 does not extend all the way to the expression kit side of the connector 6, a gap is present between the barrier portion 26 and the entrance of the air tube 62. As a consequence, any milk passing through the barrier portion 26 falls down inside the connector 6 under the influence of gravity at the position of the gap. The milk is then retained in the milk collector 61 of the collector 6, which is located at a lower level than the entrance of the air tube 62. Preferably, the expression kit connector 6 is at least partially made of transparent material so that the user of the breast pump device 1 may actually see the milk in case leakage has occurred.

Likewise, the vacuum unit connector 7 comprises an air tube 72 extending from an inside space 73 of the connector 7 to outside of the connector 7. Interconnecting the hose 5 and the vacuum unit connector 7 involves inserting the air tube 72 in an end of the hose 5. When the connector 7 is arranged on the vacuum unit 3 and the breast pump device 1 is operated, air is drawn towards the vacuum unit 3 through the hose 5 and the air tube 72. The air tube 72 does not extend all the way to the vacuum unit side of the connector 7, so that the air is released from the air tube 72 in the inside space 73 of the connector 7. In the configuration as shown, the air tube 72 has a central arrangement in the connector 7, whereas an air inlet 35 of the vacuum unit 3 has a non-central arrangement in an area 36 of the vacuum unit 31 that is configured to receive the connector 7, and is located at a higher level than the air tube 72 of the connector 7 when the connector 7 is in place in the area 36 as mentioned. As a consequence of the fact that the air inlet 35 of the vacuum unit 3 is not aligned with the air tube 72 of the connector 7, but is located at a higher level instead, any milk that may have travelled all the way down to the vacuum unit connector 7 falls down inside the connector 7 under the influence of gravity as soon as it exits the air tube 72. The milk is then retained in the milk collector 71 of the collector 7, which is located at a lower level than the exit of the air tube 72. Preferably, the vacuum unit connector 7 is at least partially made of transparent material so that the user of the breast pump device 1 may actually see the milk in case leakage has occurred.

It follows from the foregoing that, according to the invention, a breast pump device 1 is realized that is safe and easy to use. Milk leakage from the expression kit 2 towards the hose 5 and the vacuum unit 3 is prevented by means of the barrier portion 26 as arranged at the position of the air outlet 27 of the expression kit 2, through which the air that is drawn from the breast-receiving funnel 23 towards the vacuum unit 3 under the influence of the pump 31 passes. In case some droplets of milk enter the barrier portion 26 and have a clogging effect on the barrier portion 26 as a consequence thereof and/or in case some droplets of milk are drawn through the barrier portion 26 by an ongoing pumping action, aspects of the behavior of the motor 32 for driving the pump 31 are influenced, and the insight that this happens is used for terminating operation of the motor 32 as soon as a too large deviation of one or more operational characteristics of the motor 32 is found. The process of determining whether the motor 32 should be switched off involves detecting one or more operational characteristics of the motor 32 and processing detected information in the controller 33, particularly comparing detected information to an appropriate reference and assessing whether a deviation is found that is larger than a predetermined maximum. Unlike known prior art solutions, there is no need to apply a sensor for detecting the presence of liquid at a suitable position in the breast pump device 1.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

The invention claimed is:

1. A breast pump device for extracting breast milk from a human breast, comprising:
   an expression kit comprising a breast-receiving funnel, a milk outlet, an air outlet, and a milk leakage preventing arrangement associated with the air outlet, constituting a barrier to human breast milk while allowing air to pass,
   a vacuum unit comprising an air inlet, a pump for sucking air from the breast-receiving funnel of the expression kit, through the air outlet of the expression kit and the air inlet of the vacuum unit, and an electric motor for driving the pump,
   a conduit for establishing an air path between the air outlet of the expression kit and the air inlet of the vacuum unit, and
   a control system for controlling operation of the motor for driving the pump, the control system being configured to detect at least one operational characteristic of the motor, to make a comparison, throughout operation of the breast pump device, between the detected at least one operational characteristic and a reference of the at least one operational characteristic related to expected motor behavior based on an assumption of a certain input voltage and a normal condition of the breast pump device, which involves a certain air volume to be evacuated by the pump, and to terminate power supply to the motor when it follows from the comparison that a deviation of the at least one operational characteristic from the reference is larger than a predetermined maximum deviation for indicating a clogging effect on the milk leakage preventing arrangement by droplets of milk entering the milk leakage preventing arrangement and/or that droplets of milk are drawn through the milk leakage preventing arrangement by an ongoing pumping action.

2. The breast pump device according to claim 1, wherein the control system is configured to detect at least one of an electric current drawn by the motor and a rotational speed of the motor.

3. The breast pump device according to claim 1, wherein the control system is configured to use a detected value of the at least one operational characteristic as a reference for a next detected value of the at least one operational characteristic.

4. The breast pump device according to claim 1, wherein the reference involves a reference curve of the at least one operational characteristic over time, and wherein the control system is configured to determine a curve of the detected at least one operational characteristic over time, to make a comparison of the detected curve and the reference curve, and to terminate power supply to the motor when it follows from the comparison that a deviation of the detected curve from the reference curve is larger than a predetermined maximum deviation.

5. The breast pump device according to claim 4, wherein the control system is configured to determine the reference curve of the at least one operational characteristic over time in relation to an input voltage curve of the motor over time.

6. The breast pump device according to claim 1, comprising at least one milk collector for receiving and collecting any milk leaking from the expression kit, the milk collector being located beyond the milk leakage preventing arrangement associated with the air outlet of the expression kit, as seen from the breast-receiving funnel of the expression kit.

7. The breast pump device according to claim 6, comprising connectors for arrangement at the respective ends of the conduit, one of the connectors being configured to connect the conduit in an airtight manner to the air outlet of the expression kit, and the other connector being configured to connect the conduit in an airtight manner to the air inlet of the vacuum unit, wherein the milk collector comprises a room in at least one of the connectors.

8. The breast pump device according to claim 7, wherein the at least one connector comprising the milk collector is designed for having the room of the connector located at a lower level than an entrance of an air tube.

9. The breast pump device according to claim 7, wherein the connector that is configured for connecting the conduit in an airtight manner to the air inlet of the vacuum unit is designed to connect to the conduit at a central area of the conduit, and wherein the air inlet of the vacuum unit is arranged at a higher level than a center of an area of the vacuum unit that is configured to receive the connector.

10. The breast pump device according to claim 7, wherein the at least one connector comprising the milk collector is at least partially made of a transparent material.

11. The breast pump device according to claim 1, wherein the milk leakage preventing arrangement associated with the air outlet of the expression kit is hydrophobic and comprises a solid sheet of material, the sheet being provided with holes.

12. The breast pump device according to claim 1, wherein the milk leakage preventing arrangement associated with the air outlet of the expression kit is hydrophobic and comprises a porous membrane.

13. The breast pump device according to claim 1, wherein the milk leakage preventing arrangement associated with the air outlet of the expression kit is hydrophobic and comprises a labyrinth.

14. The breast pump device according to claim 1, wherein controlling operation of the motor for driving the pump comprises controlling a supply of electric power to the motor.

15. A breast pump device for extracting breast milk from a human breast, comprising:
   an expression kit comprising a breast-receiving funnel, a milk outlet, an air outlet, and a milk leakage preventing arrangement associated with the air outlet, constituting a barrier to human breast milk while allowing air to pass,
   a vacuum unit comprising an air inlet, a pump for sucking air from the breast-receiving funnel of the expression kit, through the air outlet of the expression kit and the air inlet of the vacuum unit, and an electric motor for driving the pump,
   a conduit for establishing an air path between the air outlet of the expression kit and the air inlet of the vacuum unit, and
   a control system for controlling operation of the motor for driving the pump, the control system being configured to: detect at least one operational characteristic of the motor, to make a comparison between the detected at least one operational characteristic and a reference of the at least one operational characteristic throughout operation of the breast pump device, terminate power supply to the motor when it follows from the comparison that a deviation of the at least one operational characteristic from the reference is larger than a predetermined maximum deviation; and the control system is configured to determine an actual value of the reference of the at least one operational characteristic in relation to an actual input voltage of the motor.

16. The breast pump device according to claim 15, wherein the control system is configured to detect at least one of an electric current drawn by the motor and a rotational speed of the motor.

17. The breast pump device according to claim 15, wherein controlling operation of the motor for driving the pump comprises controlling a supply of electric power to the motor.

18. The breast pump device according to claim 15, wherein the reference involves a reference curve of the at least one operational characteristic over time, and wherein the control system is configured to determine a curve of the detected at least one operational characteristic over time, to make a comparison of the detected curve and the reference curve, and to terminate power supply to the motor when it follows from the comparison that a deviation of the detected curve from the reference curve is larger than a predetermined maximum deviation.

19. The breast pump device according to claim 18, wherein the control system is configured to determine the reference curve of the at least one operational characteristic over time in relation to an input voltage curve of the motor over time.

20. The breast pump device according to claim 19, comprising connectors for arrangement at the respective ends of the conduit, one of the connectors being configured to connect the conduit in an airtight manner to the air outlet of the expression kit, and the other connector being configured to connect the conduit in an airtight manner to the air inlet of the vacuum unit, wherein a milk collector comprises a room in at least one of the connectors.

21. The breast pump device according to claim 15, comprising at least one milk collector for receiving and collecting any milk leaking from the expression kit, the milk collector being located beyond the milk leakage preventing arrangement associated with the air outlet of the expression kit, as seen from the breast-receiving funnel of the expression kit.

* * * * *